United States Patent [19]

Weeks

[11] Plant 4,714

[45] May 12, 1981

[54] ROSE PLANT

[76] Inventor: O. L. Weeks, 4759 Philadelphia St., Chino, Calif. 91710

[21] Appl. No.: 140,117

[22] Filed: Apr. 14, 1980

[51] Int. Cl.[3] ..... A01H 5/00

[52] U.S. Cl. ..... Plt./27

[58] Field of Search ..... Plt./26-27

*Primary Examiner*—Robert E. Bagwill
*Attorney, Agent, or Firm*—Vincent G. Gioia

[57] ABSTRACT

A new floribunda rose variety of unusual red and yellow coloring.

1 Drawing Figure

1

The present invention relates to a new and distinct variety of rose plant of the floribunda rose class, which was originated by my crossing as seed parent the rose known as "Plain Talk" and the rose known as "Angel Face" as pollen parent.

Among the novel characteristics possessed by this new variety which distinguish it from its parents and all other varieties of which I am aware are its unusual flower coloring and unusual coloring of individual petals. The petals begin as Spinel red and Naples yellow and lighten to Neyron red and paler yellow. The flowers are borne in clusters of three to four blooms and sometimes singly. Asexual reproduction by budding of the new variety as performed in San Bernardino County, Calif., shows that the foregoing and other distinguishing characteristics come true to form and are established and transmitted through succeeding propagations.

The new and improved rose variety which I have developed is an unusually fine floribunda rose with blooms of high centered, hybrid tea-like form displayed on a bushy, upright, free branching plant. The flowers are of medium petalage and the unusual coloring holds well upon aging, although lightening somewhat, and the open blooms retain their novel dual coloring.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "41D" is plate 41D of the Royal Horticultural Society Color Chart.

Parentage: Seedling.
*Seed parent.*—"Plain Talk".
*Pollen parent.*—"Angel Face".
Class: Floribunda.

The following observations are made of specimens grown outdoors in San Bernardino County, Calif., during the month of October.

1. FLOWER

Blooming habit: Intermittent to continuous.

A. Bud:
(1) *Size.*—Small.

2

(2) *Form.*—Ovoid.
(3) *Color.*—When sepals first divide — 41D. When petals begin to unfurl — underside of petals — pale yellow coloring (20B) of the portion of the petals at the point of attachment washes into the Spinel red (54C to 54B) petal edge.
(4) *Sepals.*—Simple, fall quickly, recurve downward, ordinary.
(5) *Peduncle.*—Length — short with some short hairs. Aspect — straight. Strength — erect. Color — 138A.

B. Bloom:
(1) *Size.*—Average size when fully expanded — about 2½to 3-inches.
(2) *Borne.*—Singly and in small clusters.
(3) *Form.*—High centered slightly flaring outer petals reflex downward, becoming flat upon opening.
(4) *Petalage.*—Number of petals under normal conditions — about 24 to 30.
(5) *Color.*—Flowers ⅓ to ½ open display bicoloring of the top surface of individual outer petals. The predominant color is Spinel red 54A to B with a portion (¼) of each petal from the point of attachment being near to Naples yellow 11C. Undersurface of petals has similar bicoloring though somewhat paler. As flowers open fully the Spinel red lightens to Neyron rose 55B to 55C. The pale yellow inner portion of the petals at the point of attachment lightens further to 158 C or D. The fresh, fully open blooms feature a golden yellow center (of the stamens and pollen) within a surrounding Neyron red circular outline separated by the pale yellow-white ring formed by the inner petal sections.

C. Petals:
(1) *Texture.*—Moderately thick.
(2) *Appearance.*—Satiny.
(3) *Form.*—Obovate, flat outer edge.
(4) *Arrangement.*—Regularly arranged.
(5) *Petaloids in center.*—Few.
(6) *Persistence.*—Drop off cleanly.
(7) *Fragrance.*—Slight.
(8) *Lasting quality.*—Long lasting on plant and as cut flower.

2. REPRODUCTIVE ORGANS

A. Stamens, filaments and anthers:
(1) *Arrangement.*—Many, regular, most filaments with anthers.
(2) *Color.*—22A.

B. Pollen: Color — 22A.
C. Styles: Uneven, short, bunched.
D. Stigmas: Color — yellow.
E. Hips: None observed.

3. PLANT

A. Form: Upright, bushy.
B. Growth: Vigorous, free branching.
C. Foliage: Compound 3 to 7 leaflets.
(1) *Size.*—Small.
(2) *Quantity.*—Abundant but scattered.
(3) *Color.*—New foliage: Upper side — near to 178A with green. Under side — near to 178A with green. Old foliage: Upper side — near 131A. Under side — near 139B.
(4) *Shape.*—Ovoid.
(5) *Texture.*—Upper side is glossy and under side is dull.
(6) *Edge.*—Serrated.
(7) *Serration.*—Fine.
(8) *Leaf stem.*—Color — near to 139B. Under side — 139C.
(9) *Stipules.*—Long.

(10) *Resistance to disease.*—Mildew — good. Rust — good.
D. Wood:
(1) *New wood.*—Color — near 139B. Bark — smooth, shiny.
(2) *Old wood.*—Color — near 139A. Bark — smooth, shiny.
E. Thorns:
(1) *Thorns.*—Quantity (main stalk): ordinary. On laterals from stalk — few. Form — normal. Length — medium. Color — tan. Position — scattered.
(2) *Prickles.*—Few.
F. Winter hardiness: Good winter hardiness.

I claim:

1. A new and distinct variety of rose plant of the floribunda class, substantially as shown and described, characterized particularly by high centered flowers of Spinel red and yellow, borne primarily in small clusters but also singly to a stem and which retain the unusual dual coloring upon aging, but lightening to Neyron red and pale yellow.

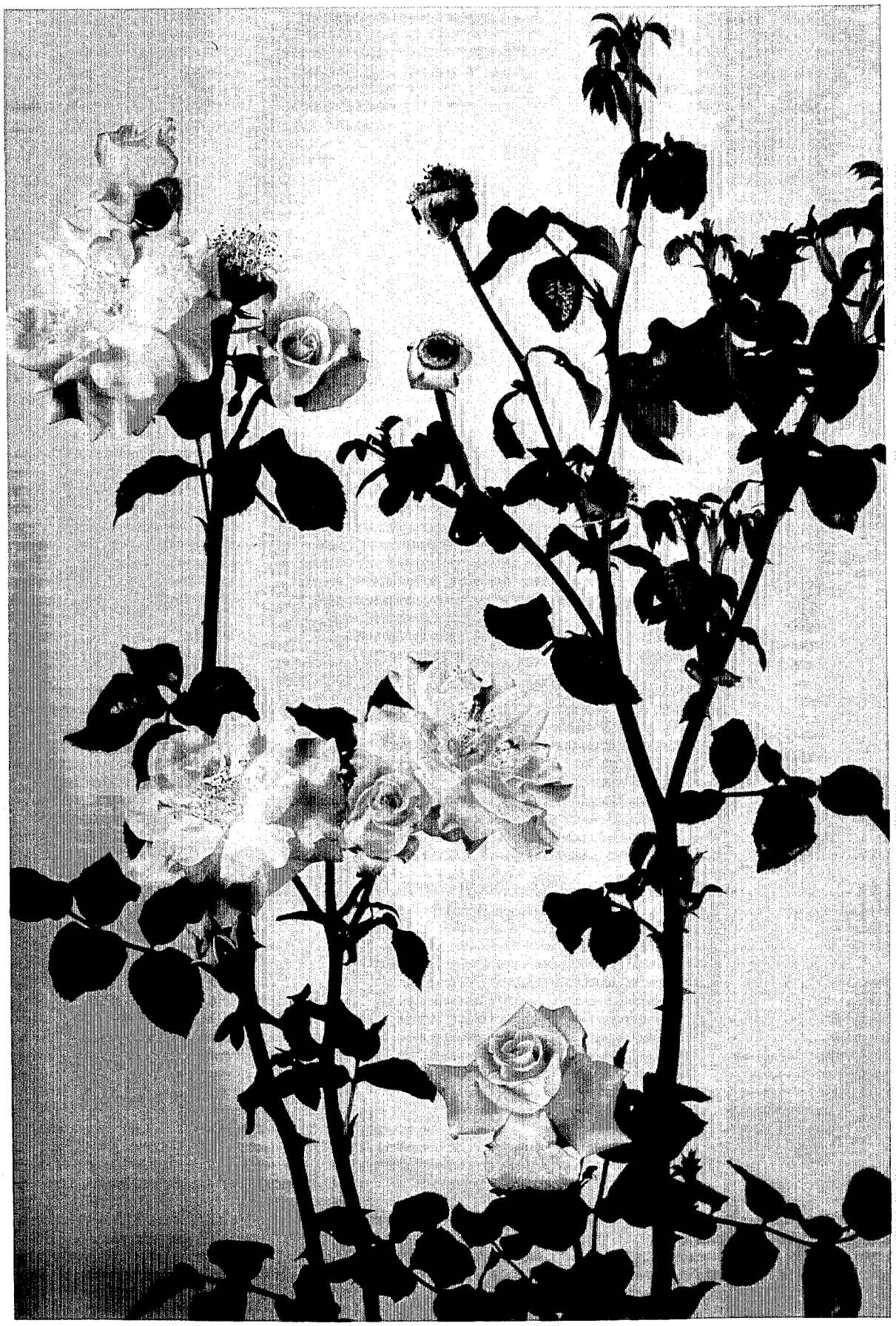

* * * * *